(12) United States Patent
Pallingen

(10) Patent No.: US 6,795,194 B2
(45) Date of Patent: Sep. 21, 2004

(54) PHOTO ELECTRIC MEASURING DEVICE

(75) Inventor: Hans Pallingen, Brixen (IT)

(73) Assignee: Viptronic GmbH, Brixen (IT)

( * ) Notice: Subject to any disclaimer, the term of this patent is extended or adjusted under 35 U.S.C. 154(b) by 211 days.

(21) Appl. No.: 10/002,398

(22) Filed: Oct. 25, 2001

(65) Prior Publication Data

US 2002/0075482 A1 Jun. 20, 2002

(30) Foreign Application Priority Data

Oct. 26, 2000 (IT) ..................................... 2000A000045
Dec. 7, 2000 (EP) ............................................ 00126468

(51) Int. Cl.$^7$ ............................................ G01N 21/47
(52) U.S. Cl. ..................................................... 356/446
(58) Field of Search ................................. 356/445–448, 356/600, 429; 256/237.2–237.5

(56) References Cited

U.S. PATENT DOCUMENTS

| | | | |
|---|---|---|---|
| 3,591,291 A | * | 7/1971 | Greer et al. ................. 356/600 |
| 4,200,397 A | * | 4/1980 | Sick et al. ................... 356/429 |
| 4,390,277 A | | 6/1983 | Quinn |
| 4,511,248 A | | 4/1985 | Abbas |
| 4,719,912 A | | 1/1988 | Weinberg |
| 5,004,339 A | | 4/1991 | Pryor et al. |
| 5,966,205 A | | 10/1999 | Jung et al. |
| 6,111,653 A | * | 8/2000 | Bucknell et al. ............ 356/446 |

FOREIGN PATENT DOCUMENTS

GB  2 082 015  2/1982

\* cited by examiner

Primary Examiner—Richard A. Rosenberger
(74) Attorney, Agent, or Firm—Weingarten, Schurgin, Gagnebin & Lebovici LLP

(57) ABSTRACT

A device for the photoelectric measuring of an opaque or transparent object to be measured includes a photoelectric sensor (4) and a measuring optics (3) which directs measuring light originating from a measurement field of the object to be measured (6) onto the sensor (4). A control electronic (5) cooperates with the sensor (4) for the processing of the electrical signals produced by the sensor. The sensor (4) includes at least two individually controlled and concentrically arranged partial sensors (41, 42, 43), and the control electronics (5) includes switching means (51) by which the partial sensors (41, 42, 43) can be selectively switched on or off-line. The use of a photoelectric sensor made of or divided into several partial sensors enables a purely electronic and therefore simple and fast selection of different effective measurement field sizes.

8 Claims, 1 Drawing Sheet

PHOTO ELECTRIC MEASURING DEVICE

FIELD OF THE INVENTION

The invention relates to a measuring device for the photo electric measuring of an object to be measured. Especially, the invention relates to a densitometer or a color measuring apparatus.

BACKGROUND ART

Measuring apparatus for the optical measurement of images or test fields on paper or films always have a fixed size measurement field. Such instruments are used mainly in the printing or photographic fields. Typical measuring apparatus are, for example, densitometers and color measuring apparatus.

The densitometer is the measuring apparatus most widely used in reproduction and printing. Densitometers are constructed as hand held apparatus, table mounted apparatus, or measuring tables, or are directly built into a production machine, for example, a printing machine for a photographic minilab. They are used with non-transparent originals for the determination of the optical color layer density (color density) of the individual color layers (cyan, magenta, yellow and black and also blue, green and red), but also for the determination of the shade value, which is a value associated with the size of the pixel, and other measured parameters derived therefrom. Shine through instruments determine color densities, pixel sizes, and derivatives thereof.

Color measuring apparatus allow the determination through measurement technology of the visual color impressions, and their quantitative description through color values in different standardized color spaces.

Optical-electronic measuring apparatus are also on the market which do not correspond with the above mentioned apparatus families, for example, built-in units in printing machines.

All these apparatus have the disadvantage of a fixed measurement field size. However, in practice an adjustable measurement field size is often desired or required. The desire for an adjustable measurement field size can have different causes, for example:

print carriers (paper, cardboard, plastic foils, and so on) with a coarse structure must be measured with a large measurement spot.

high quality printing on high-quality paper with fine details requires a small measurement spot.

coarse grids, for example, newspaper, must be measured with a large measurement spot.

the measurement of lines requires a small measurement spot.

Measurement apparatus are already known wherein the size of the measurement field can be changed by partial or complete exchange of the measurement optics. However, the manipulation of these measurement apparatus is very impractical, especially when the measurement apparatus are used in the production process or in operating printing machines. Furthermore, such apparatus are of relative costly construction and, thus, expensive.

SUMMARY OF THE INVENTION

It is now an object of the invention to improve a device of the generic type in such a way that at least two different measurement field sizes are available, which can be chosen without movement or exchange of mechanical and/or optical components (lens components).

The solution of the object underlying the present invention is achieved with a measurement device in accordance with the invention, including a photoelectric sensor, which has at least two individually controllable sensor portions (partial sensors), and a switching means for selectively activating and deactivating the individual sensor portions.

According to the basic main aspect of the present invention, the photoelectric sensor is divided into two or more concentrical partial sensors which can be selectively connected to a control electronic so that a more or less large effective measurement field is captured. The control electronic cooperates with the sensor for processing the electric signals produced by the sensor. The selection of the different measurement field sizes can thereby be carried out without moveable mechanical and optical components and purely electronically, whereby the high speed switching from one to the other measurement field size is possible.

BRIEF DESCRIPTION OF THE DRAWINGS

The invention will be more fully described in the following by way of example only and with reference to the drawings, wherein.

DETAILED DESCRIPTION OF THE PREFERRED EMBODIMENTS

Figure 1:
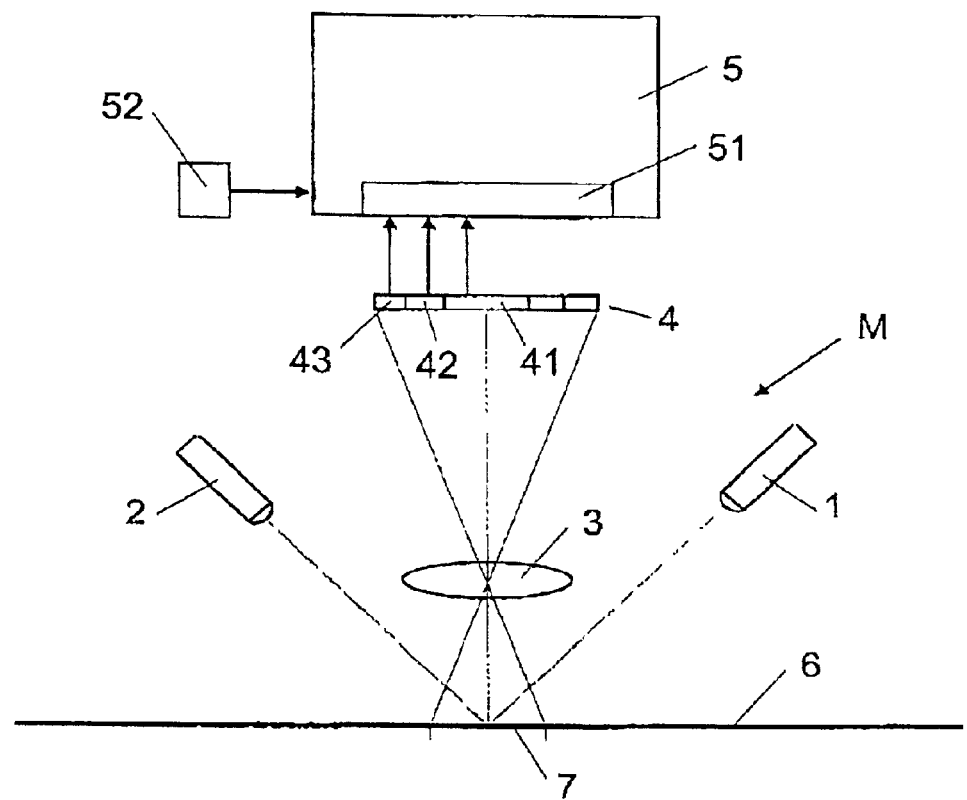
FIG. 1 is a principal schematic of a typical embodiment of the measurement device in accordance with the invention.

The measurement device, as a whole, labelled in FIG. 1 as M is constructed as a remission measurement apparatus and includes in a generally known manner a light source consisting of (in this example 2) lamps 1 and 2, measurement lens or optics 3, a photoelectric sensor 4, and a control electronic 5. As is commonplace with measurement apparatus of this type, the lamps 1 and 2 illuminate the object to be measured 6 at 45° and the measurement optics or lens 3 captures the measurement light remitted from the object to be measured at 0° and exposes the sensor 4 therewith. The control electronic 5 converts the analog electrical signals, which are produced by the sensor 4 and correspond to the intensity of the received light, into corresponding digital measurement values and calculates therefrom the desired measurement parameters or provides the digital measurement data to an external computer for further processing.

As described so far, the measurement device in accordance with the invention corresponds to conventional measuring devices of this type so that the person skilled in the art does not need any further description thereof. Of course, for the measurement of transparent objects to be measured, the light source must be positioned on that side of the measurement object which is away from the sensor. The light source of the measurement device can also be omitted if other illumination is present.

Figure 2:
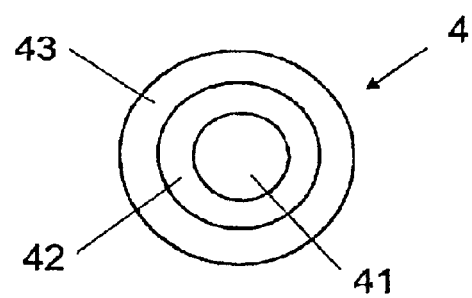
FIG. 2 is a schematic top view of a photoelectric sensor of the measurement device illustrated in FIG. 1.

The essential difference of the invention to the state of the art consists in the construction of the photoelectric sensor 4. In accordance with one aspect of the invention, the latter is constructed of two or more concentrically arranged partial sensors 41, 42 and 43. The innermost partial sensor 41 is circular, while the outer partial sensors 42 and 43 are annular. This is apparent from FIG. 2. The practical realization of the partial sensors 41 to 43 can be achieved by accordingly shaped individual photodiodes or by photodiode arrangements including a corresponding circular or annular array of several or many smaller photodiodes or similar photoelectric converters.

The control electronic 5 is provided with generally known electronic switch means 51, by which the signals from the (3) partial sensors 41–43 can be selected or excluded from the further processing. The switching means 51 can be controlled in a generally known manner, for example, by operating buttons 52 or under program control.

The measuring lens or optics 3 are positioned and constructed in such in way that they image a nominal largest measurement field 7 of, for example, 3 to 5 mm diameter, over the whole surface of and focussed onto the whole sensor 4, so that the outermost partial sensor 43 is also still fully illuminated. When the control electronic 5, by way of the switching means 51, uses the signals of all partial sensors 41–43 for the forming of measuring data, an effective measurement field of (in this case) 3–5 mm diameter is measured. When the signals of the outermost or also the intermediate partial sensor 43 or 42 are not considered for the generation of the measurement data, the effective measurement field size corresponds to the ratio of the diameters of the intermediate partial sensor 42 or the inner partial sensor 41 to the outermost partial sensor 43 (relative to the outer diameter respectively).

The use of a photoelectric sensor or photoelectric converter in accordance with the invention made of several partial sensors or divided thereinto enables a purely electronic and therefore very fast selection of, or switching between, effective measurement fields of different sizes.

Of course, only two partial sensors or more than three partial sensors can be provided.

By supplementing with color selective and/or spectrally resolving electrical components, the described measuring device can be constructed in a generally known manner as a densitometer or color measuring apparatus.

What is claimed is:

1. Apparatus for the photoelectric measuring of an object to be measured, for use as a densitometer or color measuring apparatus, comprising:

a photoelectric sensor;

a measuring lens for directing measuring light originating from a measurement spot on the object to be measured to the sensor; and a control electronic cooperating with the sensor for processing electrical signals produced by the sensor;

whereby the sensor includes at least two individually controllable and concentrically positioned partial sensors and that the control electronic includes switching means for selectively switching the partial sensors on or off line.

2. The apparatus according to claim 1, wherein the sensor includes at least three partial sensors.

3. The apparatus according to claim 2, wherein the measuring optics is constructed for imaging a largest nominal measurement field over the whole surface of all partial sensors.

4. The apparatus according to claim 2, wherein the partial sensors are constructed as circular or annular photodiodes or photodiode arrangements.

5. The apparatus according to claim 2, wherein the partial sensors are constructed as a respective circular photodiode or photodiode arrangement, and at least two annular photodiodes or photodiode arrangements.

6. The apparatus according to claim 1, wherein the measuring optics is constructed for imaging a largest nominal measurement field over the whole surface of all partial sensors.

7. The apparatus according to claim 1, wherein the partial sensors are constructed as circular or annular photodiodes for photodiode arrangements.

8. The apparatus according to claim 1, wherein the partial sensors are constructed as a respective circular photodiode or photodiode arrangement, and at least one annular photodiode or photodiode arrangement.

* * * * *